United States Patent [19]

Tomantschger et al.

[11] Patent Number: 5,173,166
[45] Date of Patent: Dec. 22, 1992

[54] ELECTROCHEMICAL GAS SENSOR CELLS

[75] Inventors: Klaus Tomantschger, Mississauga, Canada; Allan A. Janis; Norman L. Weinberg, both of Amherst; Joseph M. Rait, Buffalo, all of N.Y.

[73] Assignee: Minitech Co., Buffalo, N.Y.

[21] Appl. No.: 513,441

[22] Filed: Apr. 16, 1990

[51] Int. Cl.$^5$ .......................................... G01N 27/416
[52] U.S. Cl. .................................. 204/412; 204/425; 204/426; 204/427; 204/431
[58] Field of Search ............... 204/431, 432, 412, 424, 204/425, 426, 427

[56] References Cited

U.S. PATENT DOCUMENTS

| | | | |
|---|---|---|---|
| 4,025,412 | 5/1977 | LaConti | 204/195 |
| 4,227,984 | 10/1980 | Dempsey et al. | 204/408 |
| 4,394,239 | 7/1983 | Kitzelmann et al. | 204/414 |
| 4,522,690 | 6/1985 | Venkatasett | 204/153.19 |
| 4,543,273 | 9/1985 | Handa et al. | 427/126.3 |

*Primary Examiner*—John Niebling
*Assistant Examiner*—William T. Leader
*Attorney, Agent, or Firm*—Donald E. Hewson; E. Herbert Liss

[57] ABSTRACT

An electrochemical gas sensor cell is provided, the use of which permits quantitative measurement of volatile gas contaminants in an atmosphere being monitored, generally at ambient temperatures below 100°C. The cell comprises at least a first sensor electrode and a second counter electrode, on either side of an electrolyte which may be immobilized in a matrix, or a polymer electrolyte. The sensing electrode has a catalyst dispersed on a porous base, and is mounted in such a manner as to be exposed to the atmosphere which is to be sensed for gaseous contaminants, with the counter electrode being isolated from any exposure to that atmosphere. Generally, the electrodes are mounted in electrically conductive plastic frames, sandwiching a third non-conductive frame member in which the electrolyte is located. In an alternative embodiment, a further reference electrode may be mounted so as to be exposed to the electrolyte. The porous electrode may comprise a porous base layer, a catalytically active metal (usually a noble metal), carbon, and a polymeric hydrophobic binder.

32 Claims, 3 Drawing Sheets

ELECTROCHEMICAL GAS SENSOR CELLS

FIELD OF THE INVENTION

This invention relates to electrochemical gas sensor cells. In particular, the invention relates to gas sensor cells which, by the choice of catalyst and electrolyte, may be used in circumstances to sense the presence of a gas contaminant in an atmosphere, especially in instances where the temperature of the atmosphere is below 100° C. The electrochemical gas sensor cell has a specific potential developed between a sensor electrode and a counter electrode or a reference electrode, which potential will be indicative of the amount of the gas contaminant that is present. The present invention also teaches porous electrodes whose use in the gas sensor cells makes them particularly effective.

BACKGROUND OF THE INVENTION

In human inhabited environments, and in environments where other dangers such as explosion, fire or toxicity may occur, there is very often a requirement to test for gas contaminants which may create a potential hazard. In particular, there is an increasing demand for devices to monitor a specific atmosphere—generally an enclosed volume—for toxic or flammable gases. Also, particularly where the atmosphere being monitored is inhabited by humans, there is a specific requirement for sensors having a rapid and reliable response to such contaminating gases as carbon monoxide, oxides of nitrogen, sulfur dioxide, hydrogen sulphide, carbon dioxide, hydrogen, phosphine, arsine, methanol, volatile hydrocarbons, and so on. Any such gas requires a specific sensor cell design, and in any given installation there may be several sensor cells according to the present invention installed, having electrolytes and catalysts chosen for each of the sensor cells to be reactive to the presence of specific contaminating gases being tested for.

In some circumstances, the enclosed volume being monitored may be monitored only for one or two specific contaminating gases, which gases are the only likely gas contaminants to occur in such atmosphere being monitored. An example may be storage rooms where hazardous chemicals may be kept, or production facilities where hazardous materials are being released or are being used in the manufacture of other materials, where the possible gas contaminants are known and specific cell systems may thereby be designed.

To satisfy the requirement to be able to monitor for the presence of gas contaminants, it is necessary not only that sensor cells be provided that are capable of being economically produced and therefore readily purchased, it is also necessary that such sensor cells shall have a reasonably long active lifetime when installed in place. Moreover, particularly where it is necessary to monitor for toxic or flammable gases where there may be humans in the environment being monitored, or where there is a specific hazard, such sensor cells must be capable of detecting the presence of low concentrations of contaminant gases being tested for, so as to provide sufficient warning before the concentration of contaminant gas reaches dangerous levels.

The present invention provides gas sensor cells that have a catalytically active sensor electrode which is exposed to the atmosphere being monitored; where the sensor electrode is separated from a counter electrode which may also function as a reference electrode, or a counter electrode and a reference electrode, by a suitable ion conductive electrolyte. The nature of the electrolyte, and the manner in which it is retained in position, is discussed hereafter. It is important, however, that the sensor electrode must be sufficiently sensitive to low concentrations of gas contaminants in the atmosphere being tested, and examples of such electrodes are discussed hereafter.

Often, the counter electrode is structurally identical to the sensing electrode, but it need not be. In general, the counter electrode is exposed to an enclosed volume of scrubbed or uncontaminated air or other suitable gas, or a known concentration of the gas contaminant in air or other suitable gas, depending on the cell system being used and the gas contaminant being tested for.

The present invention provides a structure for the electrochemical gas sensor cells which is essentially of a sandwich-type construction, where the outer frame members secure the electrodes in place, and sandwich a third frame member between them in which the electrolyte is located. In the usual embodiments, the outer frame members are loaded with an electrically conductive additive, so as to exhibit specific conductivity characteristices, and thereby providing means for connecting external electrical measuring means (or, in yet another alternative embodiment, an external voltage source) directly to the sensor cell frame members. Moreover, the outer frame members of the electrochemical sensor cell of the present invention provide means for sealing the structure together, and thereby sealing means for the electrolyte chamber, as discussed hereafter.

Among the gases that may be tested for are gases and volatile substances as diverse as carbon monoxide, carbon dioxide, oxides of nitrogen, oxides of sulfur, hydrides of nitrogen such as ammonia and hydrazine, hydrides of phosphorus, sulfur, arsenic or boron, mercaptans, aldehydes, hydrogen, unsaturated and saturated hydrocarbon vapours, halocarbons and alcohols such as methanol. Indeed, in general a specific cell system can be devised using suitable catalysts and electrolytes to test for any toxic, combustible or flammable gas, or generally volatile substances which may be oxidizable. The enclosed volumes within which such gas contaminant monitoring may take place include those suggested above, and as well ordinary residential housing, parking garages of all sorts, vehicles, interiors of commercial or industrial buildings, hospitals, and mines.

Prior art devices have included various patented devices such as those described below; and in any event the prior art may generally be defined as comprising electrochemical sensors, ionization chamber sensors, photoelectric types of sensors, and metal oxide semiconductor devices. Most prior art sensors are solid state or solid electrolyte, and may employ stabilized zirconia, yttria and tin oxides. However, any sensor that has heretofore been used for monitoring and/or controlling gas atmospheres has exhibited one or more of the following disadvantageous chrcteristics: (a) they most often have quite complex structures; (b) they very often must operate or can only operate at elevated temperatures (e.g. from 150° to 600° C.); (c) as well, or as a consequence of the above, they may require outside sources of electrical energy and/or heat to maintain their operating temperatures; (d) it follows that such devices may have long start-up or warm-up periods before reaching their operating characteristics; (e)

moreover, nearly all prior art devices are costly to build and/or to operate; (f) and finally, the prior art devices are subject to deterioration over time, due to gas poisoning of their sensing systems and/or sensing elements.

Several specific prior art gas sensing elements or cells are as follows:

LaCONTI 4,025,412 describes a gas sensor which is capable of detecting oxidizable gases in air. The sensor cell is a laminated filter design, in which approximately ten components are used, placed on top of one another. The assembly is held in place by mounting screws. The LaConti assembly is very expensive to produce, even in quantities, and the structure is susceptible to electrolyte leakage.

DEMPSEY et al, 4,227,984 provide a gas sensor having a solid polymer electrolyte, and being arranged so that a fixed potential difference between the reference and sensing electrodes is present at all times. The particular purpose of the Dempsey et al structure is to preclude the necessity for temperature compensation.

KITZELMANN et al, 4,394,239 teach an electrochemical sensor which is particularly adapted for detecting carbon monoxide. The electrochemical cell is enclosed in a plastic body, which serves only as a cell housing. Electrical connections are achieved by means of wires which are attached to the metal mesh embedded in the sensor and reference electrodes. Moreover, the acidic electrolyte is corrosive, thus expensive metals such as platinum have to be used as current collectors and electrical leads, resulting in increased costs. However, such metals are hydrophilic, which may result in electrolyte loss.

VENKATASETTY, 4,522,690, in a structure intended particularly for sensing the presence of carbon monoxide, require the use of a gelled aprotic organic non-aqueous electrolyte, together with platinum sensor and counter electrodes, and a silver reference electrode. Such a structure is extremely expensive to produce, even in quantities.

HANDA et al, 4,543,273 teach a structure for sensing carbon monoxide, where a solid oxide electrolyte is used. The patent, however, relates particularly to the production of the sensing element, at very high temperatures (above 600° C).

In contradistinction to the above, the present invention provides sensitive electrochemical cells, and the electrodes for use therein, which will detect the presence of low concentrations of contaminating gases—usually oxidizing gases—in air or other environments where there may be a possibility of dangerous or hazardous accumulations of such contaminating gases. These cells and their electrodes, have the following advantageous characteristics: (a) the structures, and their production, are simple; (b) they operate at ambient temperatures, which may be room temperature or in any event below 100° C.; (c) they have a fast response time; (d) they have a high activity level, by which they may become active in the presence of very low concentrations of contaminating gas; (e) they are stable in their operation; (f) they have a long operating life; (g) and finally, they are inexpensive to produce.

The present invention provides an electrochemical gas sensor cell for quantitative measurement of gas contaminants in an atmosphere being monitored, where the temperature of that atmosphere is generally below 100° C. The gas sensor cell has a first sensor electrode mounted in a first frame member, a second counter electrode mounted in a second frame member, and a third frame member which contains an electrolyte chamber, where the first and second frame members are at opposite sides, respectively, of the third frame member and the electrolyte is contained in the electrolyte chamber. The manner in which the electrolyte is retained is such as to substantially accommodate changes in temperature or humidity of the atmosphere. Each of the first, second, and third frame members are formed of a plastics material which is inert and impervious to the electrolyte—such as polypropylene, polyvinylidene difluoride, or acrylonitrile butadiene styrene (ABS), any of which may be filled with carbon or graphite.

Each of the first sensor electrode and the second counter electrode is a porous electrode, with the first sensor electrode and optionally the second counter electrode having a catalyst dispersed thereon.

The sensor electrode is mounted in the first frame member so as to be exposed to the atmosphere being monitored, and the counter electrode is mounted in the second frame member so as to be isolated from any exposure to that atmosphere. Conductor means are associated with each of the first and second electrodes, and are connected to electrical measurement means and thence optionally to additional electrical devices such as control or warning devices.

Thus, when the atmosphere being monitored contains a gas contaminant for which the catalyst on at least the sensor electrode and the electrolyte have been chosen to produce a change in the electrical potential of the sensor electrode with respect to the counter electrode in the presence of that gas contaminant, the electrical measurement means detects the change of electrical potential in such circumstances, the change of electrical potential being indicative of the presence of the gas contaminant being tested for. In that sense, the electrical potential may optionally provide a display of contaminant concentration, it may trigger a warning or control device, or it may be stored in a storage or memory device for later comparison and review.

In an alternative embodiment, a reference electrode is located so as to be exposed to the electrolyte, and potentiometric measurement means are provided between the sensor electrode and the reference electrode, as well as the electrical measurement means being between the sensor electrode and the counter electrode.

The electrolyte may be immobilized by being absorbed in a matrix contained within the electrolyte chamber, or it may be an ionically conductive solid polymer electrolyte. Moreover, the electrolyte chamber may be in communication with an electrolyte reservoir which is formed within the third frame member, above the electrolyte chamber.

Each of the first and second frame members may be electrically conductive plastics materials or suitable polymer composites, having a specific resistance value in the range of from 0.1 to 100 Ohm-cm. The materials of those frame members may be such as polypropylene, polyvinylidene difluoride, or acrylonitrile butadiene styrene (ABS), any of which may be filled with carbon or graphite.

Other suitable stable and impervious polymers include polyvinyl chloride or acrylonitrile butadiene; and other suitable electrically conductive filler materials include titanium oxide (Ebonex [TM] ceramic), and tungsten carbide. Other inert conducting polymers may be such as those described in the *Handbook of Conducting Plastics*, Volumes 1 & 2, Marcel Dekker, 1986.

In specific embodiments of the present invention, the second counter electrode may be exposed to a contained volume of cleaned or scrubbed air or other suitable gas which is substantially free of the gaseous contaminant being tested for. Moreover, in those circumstances the counter electrode is non-polarizable under ordinary operating conditions.

In a further embodiment of the present invention, the nonconducting polymer of the third frame member may have its surface plated with a suitable inert metal film such as gold, silver, platinum, or the like. In yet a further embodiment, an inert epoxy-graphite or carbon fibre composite may be used.

Galvanometric electrical measurement means may be provided, whereby a change in the voltage developed between the sensor electrode and the counter electrode may be detected and measured. The electrical measurement means may also be amperiometric.

The catalyst, or the specific catalyst for each of the sensor electrode and optionally the counter electrode, is dispersed on the porous electrode substrate in such a manner as to have a high surface area.

Still further, the present invention provides porous electrodes which may comprise at least one porous layer containing a catalytically active metal—usually a noble metal —carbon, and a polymeric hydrophobic binder. These electrodes may then be used in gas sensors according to the present invention, together with a stabilized acid liquid electrolyte or other suitable electrolyte; and are such that they may operate at ambient temperatures such as room temperature without the necessity for a prolonged start-up or warm-up period.

The present invention also provides methods for making the electrochemical gas sensor cell, where the assembly method may be such that the assembled frame members are exposed to heat at a temperature of less than about 400° C. for a predetermined period of time, depending on the polymer being used. Indeed, the methods of the present invention to provide the electrochemical gas sensor cell may be carried out at the relatively low temperature of about 165° C., or they may be carried out in an induction furnace; or when the surfaces of the frame members which face each other are coated with an iron oxide powder, the assembly may take place in a microwave oven.

Indeed, the electrochemical gas sensor cell of the present invention may be produced by injection moulding the exterior frame members around the other members of the cell which are already held in place within an injection mould.

By all of the above, the present invention provides a low cost electrochemical gas sensor cell which may be arranged by the choice of suitable and specific catalysts and electrolytes to sense low concentrations of specific gases being tested for, and provide a rapid and reliable response in the presence of such gaseous or volatile contaminant.

BRIEF DESCRIPTION OF THE DRAWINGS

All of the above is described in greater detail hereafter, in association with the accompanying drawings, which are intended for purposes of illustration only and are not intended to be indicative of the scale of any specific cell according to the present invention. In the drawings.

DESCRIPTION OF THE PREFERRED EMBODIMENTS

Figure 1:
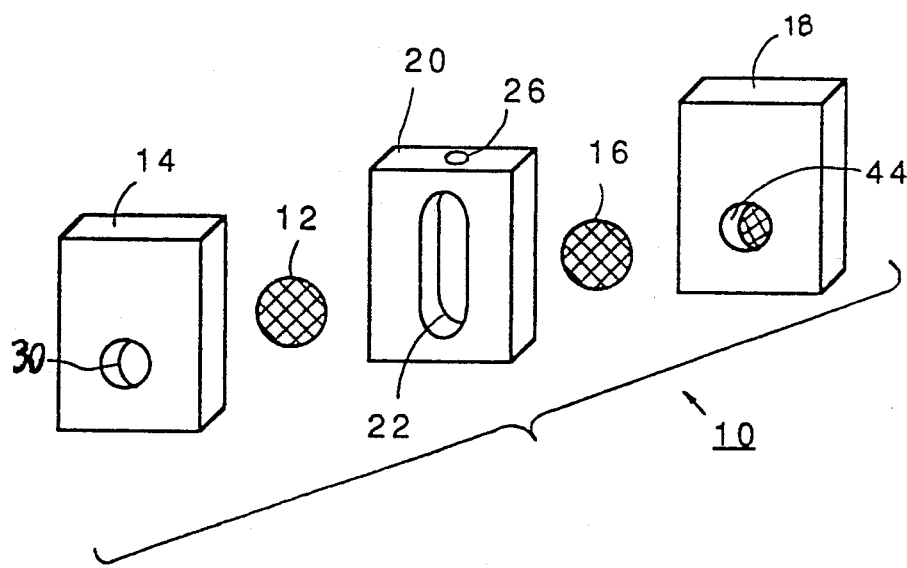
FIG. 1 is an exploded view of a typical assembly of an electrochemical sensor cell according to the present invention.

It should be noted, first, that the present invention permits the use of porous electrodes which comprise at least one porous layer containing a finely dispersed suitable catalyst. The catalyst may be a catalytically active noble metal, such as platinum, palladium, iridium etc.; or it may be an organometallic compound containing elements such as cobalt, iron or nickel; or it may be carbon or graphite, or a combination thereof; all with a suitable polymeric hydrophobic binder. The electrode structure may optionally include a metallic mesh current collector.

The basic structure of an electrochemical gas sensor cell 10, according to the present invention, is as follows: a first sensor electrode 12 is mounted in a first frame member 14, a second counter electrode 16 is mounted in a second frame member 18, and a third frame member 20 has within it an electrolyte chamber 22. An ion conductive electrolyte 24 is contained within the electrolyte chamber 22, which is defined at its sides by the first and second frame members 14 and 18 together with the sensor electrode 12 and the counter electrode 16.

The electrolyte 24 is retained within the third non-electrically conductive frame member 20 in such a manner as to substantially accomodate changes in temperature or humidity of the atmosphere. For example, the electrolyte chamber 22 may be packed with a suitable matrix such as cellulose, titanate, asbestos, or DARAMIC (TM), and then after the cell is assembled (such as by one of the modes of assembly discussed hereafter) an electrolyte may be injected into the electrolyte chamber 22 through a passage 26, after which a plug 28 may be inserted. The electrolyte may be phosphoric acid or sulphuric acid, possibly diluted with distilled water; or it may be methanesulphonic acid, or a more neutral pH electrolyte such as aqueous phosphate or sulphate salt solutions; or combinations of all of the above. Alternatively, the electrolyte may be a solid polymer electrolyte, for example a cationic or anionic resin polymer such as DuPont NAFION (TM).

In each of the embodiments shown in FIGS. 1 to 5, the sensor electrode 12 is mounted together with the first frame member 14 in such a manner that the electrode 12 is exposed to the atmosphere. That is accomodated, for example, by a passage 30 through which the gaseous atmosphere may flow as indicated at arrow 32. The counter electrode 16, on the other hand, is mounted in the second frame member 18 in such a manner that it is isolated from any exposure to the atmosphere.

Figure 3:
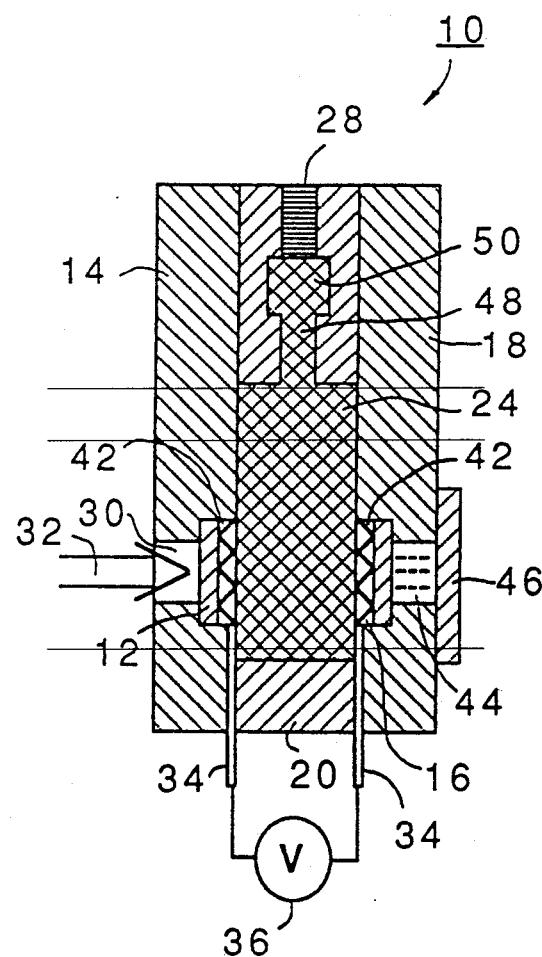
FIG. 3 shows, in schematic manner, alternative assembly features of an electrochemical cell according to the present invention.

Clearly, in order for there to be sensing of electrical potential between the electrode 12 and 16, there must be conductive means associated with them, and there must be electrical measurement means provided. In general, the material of the first and second frame members 14 and 18 is an electrically conductive plastics material, as discussed hereafter, so that they provide the conductor means away from the electrodes 12 and 16 themselves. Alternatively, conductor means such as flat wire or metallic tape 34, as indicated in FIG. 3, may be utilized. In that case, the conductors 34 are physically and electrically connected to the electrodes 12 and 16, and in that instance the first and second frame members 14 and 18 need not necessarily be themselves made of a conductive plastics material.

The electrical measurement means between the electrodes 12 and 16 may be such as a voltmeter 36; or, when the electrochemical gas sensor cell is such that it may provide a measurable current in the order of a few milliamps, for example, an ammeter 38 together with its appropriate shunt 40 may be utilized. Thus, potentiometric or galvanostatic, as well as amperiometric measuring means can be provided to sense differences in the electric potential between the sensor electrode 12 and the counter electrode 16 in the presence of a gas contaminant for which the particular cell system, including the catalysts on the electrodes 12 and 16 and the electrolyte 24, has been chosen.

In the simplest terms, in the presence of a gas contaminant as mentioned immediately above, there will be a change in the electric potential of the sensor electrode 12 with respect to the counter electrode 16, and it is that change and the detection and measurement thereof which are indicative of the presence of the gas contaminant.

The material of the first and second frame members may be an inert polymer typically comprising polypropylene, polyvinylidene difluoride, or acrylonitrile butadiene styrene (ABS), filled with carbon or graphite. Of course, the material of the first and second frame members may also be any of those discussed previously, including polyvinyl chloride or acrylonitrile butadiene styrene; and other suitable electrically conductive filler materials include titanium oxide (Ebonex [TM] ceramic), and tungsten carbide. Other inert conducting polymers may be such as those described in the Handbook of Conducting Plastics, Volumes 1 & 2, Marcel Dekker, 1986.

Typically, the electrically conductive plastics material so used has a specific resistance value which is generally in the range of from about 0.1 to 100 Ohm-cm. In a number of test cells produced in accordance with this invention, and depending on the measurement technique being used (either amperiometric or potentiometric or galvanostatic) the materials may have a specific resistance in the range of 1.0 to 10 Ohm-cm. The material of the frame members 14 and 18 may also comprise conductive plastics that are used on electronic equipment for electromagnetic interference shielding. Such material is inexpensive, easily obtained, has acceptable specific resistance values, and is stable in the temperature ranges contemplated for the electrochemical sensor cells of the present invention—up to 100° C. Typical materials include Magnex OC [TM] from Mitech Corporation, with a specific resistance of less than 1.0 Ohm-cm.; SX0.1[TM] from Polymer Concentrates, with a specific resistance of about 0.1 Ohm-cm.; and RTP-HEC[TM] from RTP Co., with a specific resistance of about 0.1 Ohm-cm., or less.

The material of the third frame member, the electrolyte frame member 20, may typically be polypropylene or ABS, which may be loaded with talcum. The material is chosen, in any event, so as to approximately match the thermal coefficient of expansion of the outer frame members.

As mentioned, the electrodes are porous, comprising at least one porous layer which may contain a catalytically active noble metal, or carbon, or they may comprise a porous or gas permeable conductive sintered matrix. Generally, the electrodes will comprise a porous layer of the catalytically active noble metal or carbon, with a polymeric hydrophobic binder such as PTFE. Such electrodes are described below.

The electrodes may also contain a metal mesh current collector, such as that indicated at 42 in FIG. 3.

Figure 2:
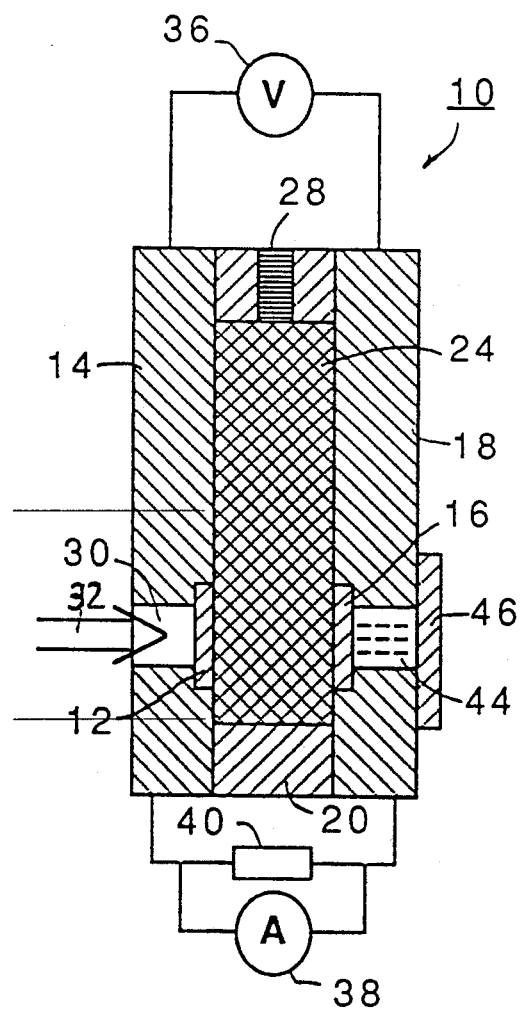
FIG. 2 is a schematic cross-section, not-to-scale, of a first embodiment of a sensor cell, showing alternative arrangements for electrical measuring means associated with the cell.
Figure 5:
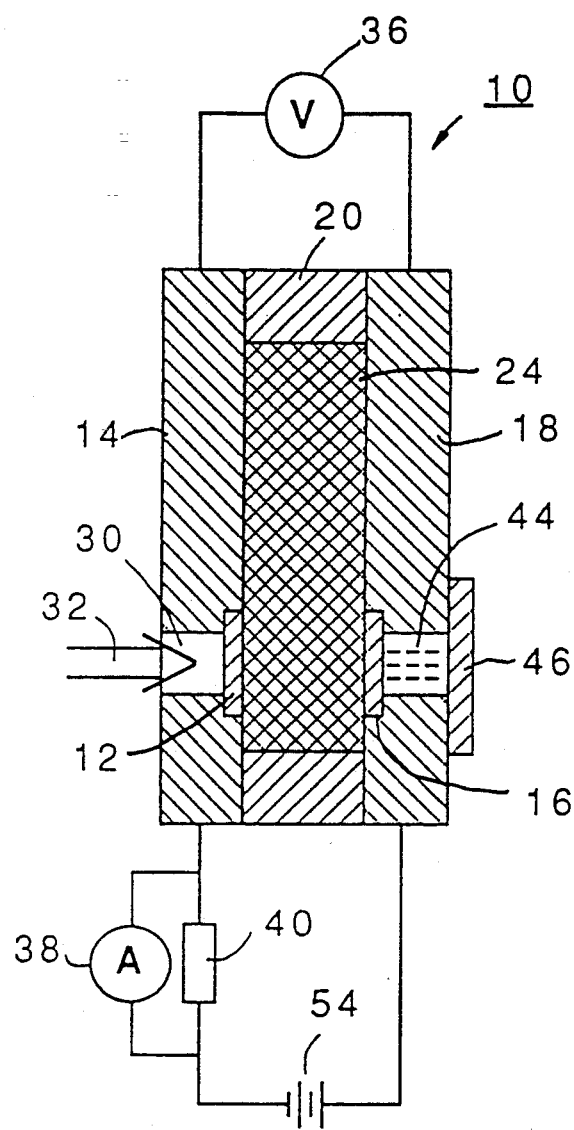
FIG. 5 shows, in schematic manner, yet a further typical embodiment of the present invention where an external voltage source is used in association with the electrochemical gas sensor cell.

By such structure, the electrochemical gas sensor cell of the present invention is essentially a fuel cell. So as to accomodate that type of arrangement, as shown in FIGS. 2, 3, and 5, the counter electrode is mounted in such a manner as to be exposed to an enclosed volume of scrubbed or otherwise uncontaminated air or gas. The gas could also be nitrogen. That is arranged by flooding the chamber 44 in the second frame member 18 with scrubbed air, after which the chamber 44 is sealed with a plug or cap 46.

An alternative arrangement for the electrolyte 24 is shown in FIG. 3, where the electrolyte chamber 22 opens into a passage 48 which communicates with an electrolyte reservoir 50. As in the structure of FIG. 2, the electrolyte chamber is sealed with a plug 28.

Figure 4:
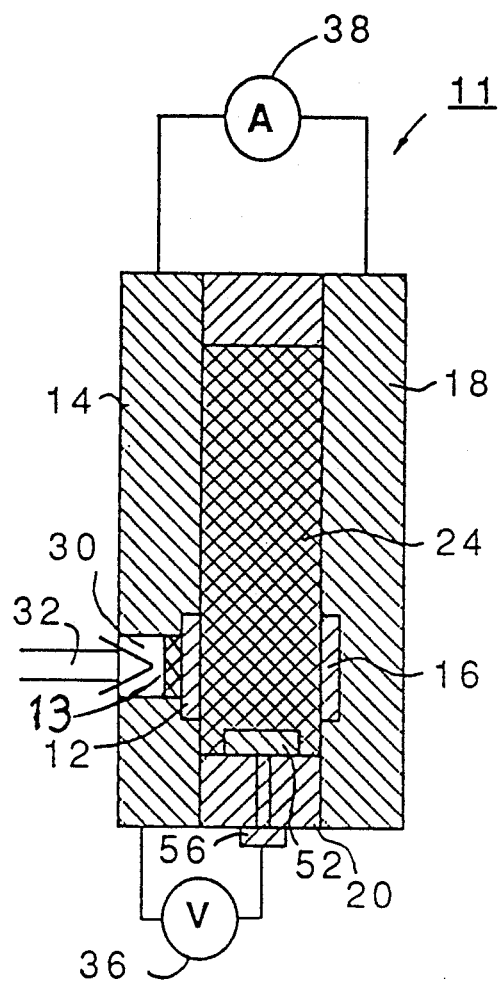
FIG. 4 shows, in schematic manner, a further typical embodiment of an electrochemical cell having a reference electrode in contact with the electrolyte.

Referring briefly to the embodiment of FIG. 4, there is shown a sensor cell 11 having an additional electrode which is reference electrode 52, together with its electrical lead or contact pad 56. That reference electrode is located within the electrolyte chamber so as to be exposed to the electrolyte 24. Potentiometric measurement means, voltmeter 36, are provided in this embodiment between the sensor electrode 12 and the reference electrode 52; other electrical measurement means—for example, the ammeter 38—are provided between the sensor electrode 12 and the counter electrode 16. It is understood, of course, that either the frame members 14 and 18 are electrically conductive, or that additional conductors are included as necessary. In any event, an additional conductor such as shown at 56 would be provided between the reference electrode 52 and the exterior of the sensor cell 11 of FIG. 4.

In yet another embodiment, as shown particularly in FIG. 5, the electrochemical gas sensor cell may be set up with an external power source 54. In that case, the external power source 54 provides a constant current flow through the sensor cell, and the voltage of the sensor electrode versus the counter or reference electrode is monitored. The ammeter 38 and shunt 40 are shown as in a test set up, to ensure a steady constant current to the sensor cell, but are not needed in an actual installation.

In the embodiment of FIG. 5, a specific voltage is developed and maintained between the sensor electrode 12 and the counter electrode 16, which is measured by the voltmeter 36. However, in the presence of a contaminant gas being tested for, the potential between the sensor electrode 12 and the counter electrode 16 will change, and that change of electrical potential is detected and is indicative of the presence and also of the concentration of the contaminant gas being tested for.

Depending on the cell system, there may be in any of the embodiments of FIGS. 2, 3, or 4, a specific electric potential developed between the sensor electrode 12 and the counter electrode 16 in the absence of the contaminant gas in the atmosphere being monitored. But, when there is a presence of the contaminant gas being tested for, there will be a predictable change of the voltage between the sensor electrode 12 and the counter electrode 16.

In other instances, there may be no or only an insignificant electrical potential developed between the sensor electrode 12 and the counter electrode 16, in the absence of a contaminant gas being tested for, and a readily detected electrical potential is developed in the presence of the contaminant.

In a two electrode structure such as that shown in FIGS. 2 or 3, the electrolyte may be a diluted sulphuric acid, in which case the material of the counter electrode 16 may comprise a storage electrode in order to obtain a stable reference voltage. That material may be lead, or oxides thereof. The cell operates, as do the others described herein, essentially as an air/metal battery with a very low capacity. But is it not the ampere-hour capacity of the cell that is a desired characteristic, it is the specific voltage between the sensor electrode and the counter electrode; so that a change of that voltage is indicative of the presence of a contaminant gas being tested for.

Generally, the rate of reaction of the electrochemical gas sensor cell is indicative of the concentration of the gas contaminant being tested for. In each instance, there is a particular anticipated voltage or trigger voltage level that should develop between the sensor electrode and the auxiliary electrode, which may be either the reference electrode or the counter electrode. In a typical circumstance, where carbon monoxide is being tested for, the presence of about 50 ppm (parts per million) could result in about 80% of the anticipated trigger voltage being reached in a period of about 5 minutes from the first exposure of the sensor electrode to that concentration. However, where the concentration is a more serious level such as 200 ppm, the response time of the cell would be within several seconds.

Several examples are given below of the manufacture of electrochemical gas sensor cells according to the present invention. In general, the gas sensor electrode 12 and the counter electrode 16 are mounted together, one on either side of and against the third frame member 20. Suitable conductive plastics materials must be chosen for the frame members 14 and 18 (or, when used, conductive wires or ribbons put in place) and a suitable nonconductive material must be chosen for the third frame member. Suitable materials have been discussed above. It is a characteristic of the present invention that the assembly of electrochemical gas sensor cells in keeping with this invention is accomplished quickly, and generally at temperatures that are less than about 300° C., or in any event less than 400° C.

Generally, the steps for assembling an electrochemical gas sensor cell according to the present invention are as follows:

a) choosing a conductive plastics material and fabricating the first and second end frame members therefrom;

b) choosing a nonconductive plastics material and fabricating the third frame member therefrom;

c) placing the material for the electrodes against the respective end frames to which the electrodes are to be bonded;

d) assembling the frame members and electrodes together; and e) exposing the assembled frame members to heat at a temperature less than about 400° C. for a predetermined period of time.

Depending on the polymer being used, for example polypropylene, step (e) may be carried out at about 165° C. for about 10 minutes, using a compression mould. Alternatively, it may be carried out in an induction furnace.

The present invention contemplates that, in some instances prior to step (d), at least one of each of the pairs of surfaces of the frame members that face each other—both surfaces of the third frame member and the inside surfaces of the first and second frame members that face them—is coated with an iron oxide powder. Then, step (e) may be carried out in a microwave oven.

Alternatively, step (a) may be carried out after step (b) and as part of steps (c), (d), and (e), by placing the third frame member and the sensor electrode and counter electrode, one at each side thereof, in a mould. Then, the material of the first and second frame members may be injected into the mould in a fluid state, and thereafter permitted to harden.

In a specific example, conductive frame members were made from polypropylene filled with carbon, by placing the conductive granulate in a compression mould, and forming at 165° C. for 5 minutes. The porous electrodes having a PTFE structure with carbon are particularly useful in the present invention, because when they are heat bonded to the first and second frames, electrical contact between the electrode and the conductive frame is assured. At the same time, because of the hydrophobicity of the PTFE, electrolyte leakage is precluded. Moreover, by using temperatures below about 300° C., and in any event below 400° C., the sintering temperature of PTFE, the structural integrity of the electrodes is assured.

After placing an electrolyte matrix in the electrolyte chamber, the electrolyte plate was sandwiched between the two outer frame members together with the electrodes, and sandwiched in a compression mould at 165° C. for 10 minutes. Thereafter, the electrolyte filling port 26 was drilled, and electrolyte injected thereinto by vacuum filling.

In another example, carbon filled gas permeable paper or cloth may be dipped into PTFE, and thereafter gold deposited so as to have a high surface area onto that substrate. Then the components of the electrochemical cell are placed in an assembly jig and transferred into an induction furnace. In that instance, the conductive plastic plates heat up and melt into the two electrode structures, producing a conductive and liquid tight bond. At the same time, the softened conductive plastic frame members attach themselves to the nonconductive electrolyte plate—the third frame member—and a well secured electrochemical cell is assembled.

In other instances, as mentioned above, the surfaces of the components that are to face one another may be painted with an iron oxide powder, for example, and then the assembly may be finished by curing in a microwave oven.

A solid polymer electrolyte sheet such as that sold in association the trade mark NAFION [TM] may have platinum electrodes sputtered, electrolessly plated, or electroplated onto it. Then, the sensor cell is formed by compression moulding at 165° C. for 10 minutes. Thereafter, the cell is activated by exposure to steam at 100° C.

Finally, an electrode paste containing platinum supported on carbon together with a polymeric binder and a solvent may be screen printed onto a cellulose electrolyte matrix, and then dried. Therafter, the cell is formed in a compression mould and activated in the manner described above.

Cells manufactured according to the various processes noted above, and in keeping with the present invention, show remarkable consistancy of performance, with rapid response in potentially dangerous concentrations of gases such as carbon monoxide. Long term operation has been demonstrated over periods of more than 12 months.

A typical cell according to the present invention may have dimensions as small as about 1.2 cm by 2.0 cm by 0.4 cm., or they may be larger or smaller.

In keeping with the present invention, the porous sensing electrodes used in the electrochemical sensing cells discussed above comprise a layer which contains a catalytically active metal—usually a noble metal—together with carbon and a polymeric hydrophobic binder, all in a suitable substrate.

The catalytic layer typically has a thickness of about 50 to 250 microns, containing the noble metal electrocatalyst. The noble metal particles in the layer are usually situated on the electrolyte side of the electrode; and the concentration of noble metal is typically less than 1.0 mg/cm2.

As used herein, the term "noble metal" is taken in its wider sense, so that it is taken to include such metals as platinum, palladium, iridium, ruthenium, rhodium, gold, silver, and alloys and mixtures of two or more such metals.

In production, the catalytically active layer of the electrode may be made particularly thin by employing such methods as rolling, spraying, or screen printing. The active layer may be applied to a suitable substrate such as carbon cloth, felt or paper; or it may optionally be applied directly to a solid electrolyte matrix such as Nafion [TM], cellulose, or Daramic [TM].

The polymeric binder may be any suitable inert resin, particularly a hydrophobic compound. Examples of such binders include polyethylene, polypropylene, polyvinylchloride, polystyrene, and PTFE. The loading of the binder may be in the range of 5 to 50% by weight of the porous electrode.

As noted, several different fabrication processes are suitable. For example, powdered carbon is mixed with a powder of a catalytically active noble metal on carbon and a binder. Catalytically active noble metal particles may be contained by 10 to 75% of the carbon particles. If desired or necessary, a pore former such as soluble salts may be incorporated in the mix, which is then typically pressed into an electrode in a suitable mold at an elevated temperature. In this manner, the pore former is removed.

It may be considered to apply a gas permeable membrane 13 at least on the gas side of the first sensor electrode as shown in FIG. 4, for example, so as to reduce exchange of water. This is because the electrolyte may tend to dilute or become too concentrated, depending on its initial electrolyte concentration, as well as being affected by such factors as the temperature and humidity of the air in the environment being sensed.

The following examples set forth various typical compositions of electrodes that have been successfully tested in the gas sensors used to measure carbon monoxide, hydrogen, and other oxidizable gases.

Example 1:
Backing:
| | | |
|---|---|---|
| Carbon Paper (Stackpole PC206 [TM]) | | 50% |
| PTFE | | 50% |

Active Layer:
| | | |
|---|---|---|
| Vulcan XC 72R [TM] | | 80% |
| PTFE | | 20% |
| Catalyst Loading: | 0.30 mg Platinum per cm2 | |

Example 2:
Backing:
| | | |
|---|---|---|
| Carbon Cloth (Stackpole Panex [TM]) | | 50% |
| PTFE | | 50% |

Diffusion Layer (Optional):
| | | |
|---|---|---|
| Acetylene Black | 25 g | 62.5% |
| PTFE | 15 g | 37.5% |
| Ammonium bicarbonate filler | 60 g | |

Active Layer:
| | | |
|---|---|---|
| Vulcan XC 72R [TM] | | 89% |
| PTFE | | 11% |
| Catalyst Loading: | 0.3 mg Gold per cm2 | |

Example 3:
Backing:
| | | |
|---|---|---|
| Carbon Paper (Stackpole P105 [TM]) | | 50% |
| PTFE | | 50% |

Active Layer:
| | | |
|---|---|---|
| Black Pearls [TM] | | 64% |
| PTFE | | 36% |
| Catalyst Loading: | 0.5 mg Palladium per cm2 | |

Example 4:
Backing:
| | | |
|---|---|---|
| Carbon Felt (Stackpole Panex CFP 30-05 [TM]) | | 50% |
| PTFE | | 50% |

Active Layer:
| | | |
|---|---|---|
| Acetylene Black | | 89% |
| PTFE | | 11% |
| Catalyst Loading: | 0.15 mg Platinum per cm2 | |

Example 5:
Backing:
| | | |
|---|---|---|
| Platinum Screen | | 50% |
| PTFE | | 50% |

Diffusion Layer (Optional):
| | | |
|---|---|---|
| Acetylene Black | 25 g | 62.5% |
| PTFE | 15 g | 37.5% |
| Ammonium bicarbonate filler | 60 g | |

Active Layer:
| | | |
|---|---|---|
| Black Pearls [TM] | | 89% |
| Graphite | | 20% |
| PTFE | | 20% |
| Catalyst Lading: | 0.50 mg Palladium/Rhodium per cm2 | |

Figure 6:
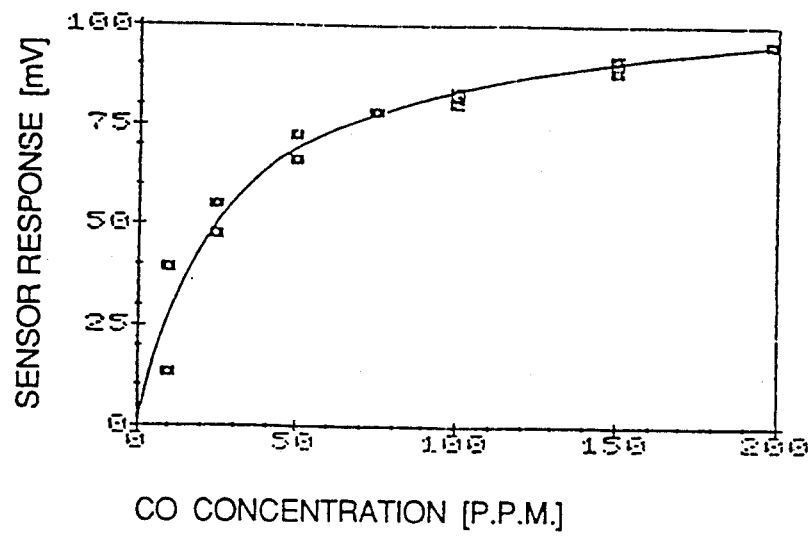
FIG. 6 shows a typical curve of potentiometric sensor output versus carbon monoxide gas concentration for a typical gas sensor cell according to this invention.
Figure 7:
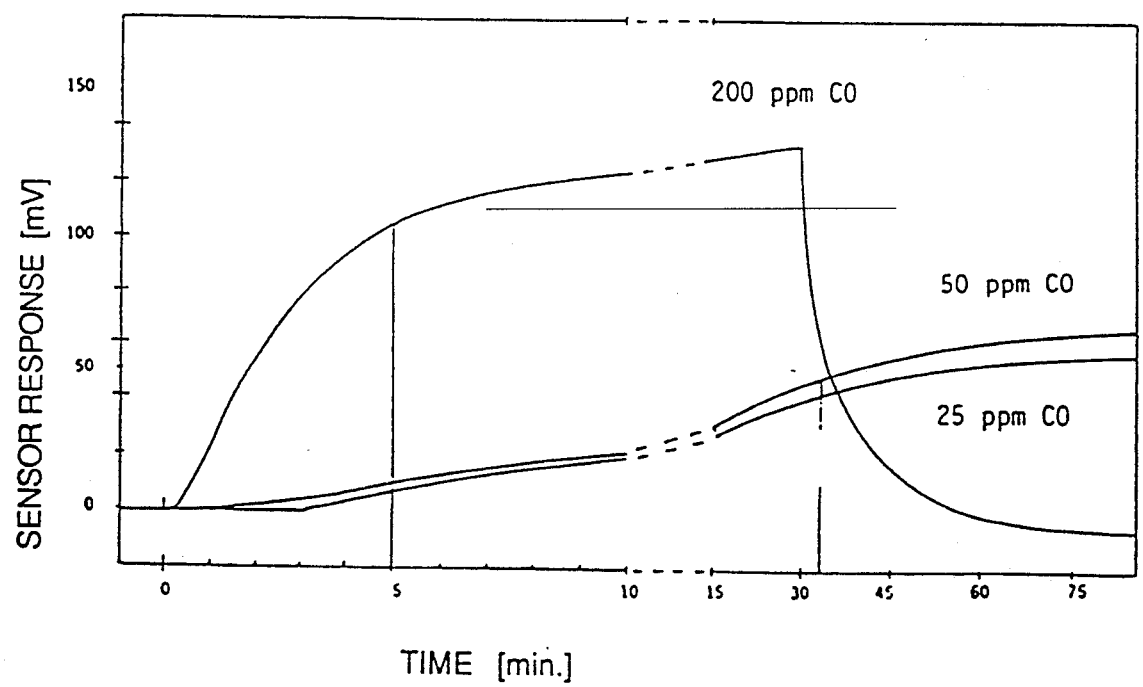
FIG. 7 shows typical response time characteristics of potentiometric sensor output for various gas contaminant concentrations.

A typical set of curves, showing the performance of a gas sensor having electrodes similar to those of Example 1 above is shown in FIGS. 6 and 7. In FIG. 6, the potentiometric response of the cell to various concentrations of CO in air is shown; and in FIG. 7 the time response to three different CO concentrations is shown. The electrolyte was phosphoric acid in each case.

It should be noted that, in each electrochemical gas sensor cell in keeping with the present invention, the catalyst material is wetted—or is at least capable of being partially wetted—by the electrolyte when it is exposed thereto. It is possible to pre-condition the cell by back-charging it—forcing current through the cell, in both directions—so as to enhance the wetting characteristics of the cell, especially one that has an aqueous electrolyte. It is also possible to add a hydrophilic substance such as carboxy methyl cellulose (CMC) to the electrode mix; or even to add a hydrophilic binder such as polysulfone.

The examples noted above are exemplary, and the structure of the electrochemical gas sensor cells described above and shown in the drawings, are exemplary and not intended to be limiting as to any specific cell. The scope of the invention is defined in the appended claims.

We claim:

1. An electrochemical gas sensor cell for quantitative measurement of gaseous or volatile contaminants in an atmosphere being monitored, said gas sensor cell comprising at least a first gas permeable porous sensor electrode mounted in a first frame member, a second gas permeable porous counter electrode mounted in a second frame member, a third electrically non-conductive frame member, an ion conductive electrolyte contained within an electrolyte chamber formed in said third frame member, said first and second electrodes and said first and second frame members being located at first and second sides, respectively, of said electrolyte such that at least a portion of each of said first electrode and said second counter electrode contact said electrolyte;

wherein at least one of said first and second frame members is electrically conductive, and conductor means is associated with the other of said first and second frame members when said other frame member is electrically non-conductive;

wherein said electrolyte is retained in said third frame member in such a manner as to substantially accomodate changes in temperature or humidity of said atmosphere;

wherein said first sensor electrode and optionally also said second counter electrode contains a catalyst;

each of said first, second, and third frame members being formed of an inert plastics material which is impervious to said electrolyte;

said sensor electrode being mounted and secured with respect to said first frame member so as to be exposed to said atmosphere, and said counter electrode being mounted and secured with respect to said second frame member so as to be isolated from any exposure to said atmosphere; and wherein each of said first and second electrodes is connected to electrical measurement means;

whereby, when said atmosphere contains a gas contaminant for which the catalyst on said sensor electrode is chosen to produce a change in electrical potential with respect to said counter electrode when said sensor electrode is exposed to said gas contaminant in the presence of the chosen ion conductive electrolyte, said electrical measurement means detects the change of said electrical potential, which thereby is indicative of the presence of said gas contaminant.

2. The electrochemical gas sensor cell of claim 1, wherein said electrolyte is immobilized by being absorbed in a matrix contained within said electrolyte chamber.

3. The electrochemical gas sensor cell of claim 2, where said first gas permeable porous electrode comprises at least a porous catalytically active layer containing particles of a catalytically active noble metal, particles of carbon, and a polymeric binder; wherein said catalytic layer has a thickness of less than 250 microns, and the loading of said catalytic metal is in the range of between 0.1 and 1.0 mg/cm$^2$; and wherein the particles of said noble metal are at least partially wetted by said electrolyte.

4. The electrochemical gas sensor cell of claim 3, where said catalytically active layer is applied onto said electrolyte matrix.

5. The electrochemical gas sensor cell of claim 1, wherein said electrolyte is a solid polymer electrolyte.

6. The electrochemical gas sensor cell of claim 1, wherein said electrolyte chamber is in communication with an electrolyte reservoir formed in said third frame member above said electrolyte chamber.

7. The electrochemical gas sensor of claim 1, wherein each of said first and second frame members is formed of an electrically conductive plastics material.

8. The electrochemical gas sensor cell of claim 7, wherein said electrically conductive plastics material has a specific resistance value in the range of 0.1 to 100 Ohm-cm.

9. The electrochemical gas sensor cell of claim 7, where said electrically conductive plastics material has a specific resistance value in the range of 1.0 to 10 Ohm-cm.

10. The electrochemical gas sensor cell of claim 7, wherein the conductive plastics material of said first and second frame members is chosen from the group consisting of polypropylene, polyvinylidene difluoride, acrylonitrile butadiene styrene, polyvinyl chloride, and acrylonitrile butadiene; and wherein said conductive plastics material is filled with a conductive filler chosen from the group consisting of carbon, graphite, titanium oxide, and tunsten carbide.

11. The electrochemical gas sensor cell of claim 1, adapted to be used at a temperature below 100° C.

12. The electrochemical gas sensor cell of claim 1, where said gas sensor cell is adapted to test for a specific gas for which the catalyst on said sensor electrode is chosen; and where said second counter electrode is exposed to a contained volume of a gas chosen from the group consisting of scrubbed air, cleaned air, and air containing a known concentration of a gas chosen from the group consisting of carbon monoxide, hydrogen sulfide, hydrogen, arsine and mixtures thereof.

13. The electrochemical gas sensor cell of claim 12, where said counter electrode is non-polarizable.

14. The electrochemical gas sensor cell of claim 1, where said electrical measurement means is potentiometric, whereby a change in the voltage developed between said sensor electrode and said counter electrode may be detected and measured by said potentiometric measurement means.

15. The electrochemical gas sensor cell of claim 1, where said electrical measurement means is amperiometric.

16. The electrochemical gas sensor cell of claim 1, further comprising a reference electrode located so as to be exposed to said electrolyte; and wherein potentiometic measurement means are provided between said sensor electrode and said reference electrode, as well as said electrical measurement means between said sensor electrode and said counter electrode.

17. The electrochemical gas sensor cell of claim 1, wherein said sensor cell is adapted to develop a specific electric potential in the absence of a contaminant gas in said atmosphere being monitored, and said specific electrical potential changes predictably in the presence of a contaminant gas.

18. The electrochemical gas sensor cell of claim 1, wherein said sensor electrode is adapted to develop a specific electric potential with respect to said counter electrode in the absence of a contaminant being tested for in said atmosphere being monitored, and a readily detected electric potential in the presence of a contaminant gas.

19. The electrochemical gas sensor cell of claim 1, further comprising an external power source connected to said first sensing electrode and said second counter electrode so as to provide a constant current flow through said sensor cell;

whereby, a voltage is developed between said first and second electrodes which is measured by said electrical measurement means;

and whereby, when said atmosphere contains a gas contaminant for which the catalyst on said sensor electrode is chosen to produce a change in electrical potential with respect to said counter electrode when said sensor electrode is exposed to said gas contaminant in the presence of the chosen ion conductive electrolyte, said electrical measurement means detects the change of said electrical potential, which thereby is indicative of the presence of said gas contaminant.

20. The electrochemical gas sensor cell of claim 1, where said electrolyte is phosphoric acid, where said catalyst is chosen from the group consisting of platinum and gold, and wherein said sensor is adapted to test for any gas chosen from the group consisting of carbon monoxide, hydrogen sulfide, hydrogen, arsine, and combustible hydrocarbons.

21. The electrochemical gas sensor cell of claim 20, where said catalyst is platinum, and wherein said sensor is adapted to test for carbon monoxide in the range of up to 200 ppm.

22. The electrochemical gas sensor cell of claim 21, where a gas permeable membrane is applied to the gas side of at least said first gas permeable porous sensor electrode so as to suppress evaporation of volatile components from said electrolyte.

23. The electrochemical gas sensor cell of claim 1, where each of said first sensor electrode and said second counter electrode comprises at least a porous catalytic layer containing particles of a catalytically active noble metal, particles of carbon, and a polymeric binder; wherein said catalytic layer has a thickness of less than 250 microns, and the loading of said catalytic metal is in the range of between 0.1 and 1.0 mg/cm$^2$; and wherein the particles of said noble metal are at least partially contacted by said electrolyte.

24. The electrochemical gas sensor cell of claim 23, where said catalytically active noble metal is chosen from the group consisting of platinum, palladium, rhodium, iridium, ruthenium, silver, gold, and alloys and mixtures thereof.

25. The electrochemical gas sensor cell of claim 23, where said catalytically active noble metal particles are contained by 10 to 75% of said carbon particles.

26. The electrochemical gas sensor cell of claim 23, where said catalytic layer has a thickness of from 25 to 250 microns.

27. The electrochemical gas sensor cell of claim 23, where said polymeric binder is a hydrophobic material chosen from the group consisting of polypropylene, polyethylene, polystyrene, polyvinyl chloride, and PTFE; and wherein the loading of said binder is in the range of 5 to 50% by weight of the porous electrode.

28. The electrochemical gas sensor cell of claim 23, where said catalytically active layer is produced by pressing, rolling, spraying, painting, or screen printing the materials thereof onto a suitable porous substrate.

29. The electrochemical gas sensor cell of claim 28, where said substrate is carbon paper or carbon cloth.

30. The electrochemical gas sensor cell of claim 1, where said gas sensor cell is adapted to test for a specific gas for which the catalyst on said sensor electrode is chosen; and where said second counter electrode is exposed to a contained volume of a gas chosen from the group consisting of nitrogen, and a gas containing a known concentration of a gas chosen from the group consisting of carbon monoxide, hydrogen sulfide, hydrogen, arsine and mixtures thereof.

31. The electrochemical gas sensor cell of claim 1, wherein the at least one of said first and second electrically conductive frame members has a specific resistance value in the range of 0.1 to 100 Ohm.cm.

32. The electrochemical gas sensor cell of claim 1, wherein the at least one of said first and second electrically conductive frame members has a specific resistance value in the range of 1.0 to 10 Ohm.cm.

* * * * *